United States Patent [19]

Shraiber et al.

[11] 3,978,714
[45] Sept. 7, 1976

[54] METHOD OF ULTRASONIC ECHO FLAW DETECTION AND DEVICE FOR EFFECTING SAME

[76] Inventors: David Solomonovich Shraiber, Leninsky prospekt, 39, kv. 100; Boris Glebovich Golodaev, 9 ulitsa Sokolinoi gory, 3, kv. 253; Boris Alexandrovich Palkin, Sirenevy bulvar, 67, korpus 2, kv. 102, all of Moscow; Leonid Mikhailovich Zakharov, Sovetsky prospekt, 14, kv. 31, Ivanteevka, Moskovskaya oblast; Mikhail Abramovich Genkin, ulitsa Bakuninskaya 8, kv. 26, Moscow; Dmitry Alexandrovich Filippov, ulitsa Saratovskaya, 18/10, kv. 138, Moscow; Anatoly Fedorovich Razumovsky, ulitsa Kantemirovskaya, 5, korpus 1, kv. 31, Moscow, all of U.S.S.R.

[22] Filed: Mar. 7, 1975

[21] Appl. No.: 556,537

Related U.S. Application Data

[63] Continuation-in-part of Ser. No. 281,010, Aug. 16, 1972, abandoned.

[52] U.S. Cl. .............................................. 73/67.8 S
[51] Int. Cl.² ........................................ G01N 29/04
[58] Field of Search ........... 73/67.7, 67.8 R, 67.8 S, 73/67.9, 71.5 (U.S.)

[56] References Cited
UNITED STATES PATENTS

| | | | |
|---|---|---|---|
| 2,751,783 | 6/1956 | Erdman | 73/67.8 |
| 3,257,843 | 6/1966 | Cowan | 73/71.5 |
| 3,529,466 | 9/1970 | Pryor et al. | 73/67.8 S |
| 3,678,736 | 7/1972 | May | 73/67.8 S |

*Primary Examiner*—Herbert Goldstein
*Assistant Examiner*—John P. Beauchamp
*Attorney, Agent, or Firm*—Haseltine, Lake & Waters

[57] ABSTRACT

In the course of checking an article, there are directed at the point on the article being checked, whereat ultrasonic oscillations generated by an ultrasonic flaw detecting transducer are applied, pulses of ultrasonic oscillations focused at this point, which pulses are sent by a side focusing ultrasonic transducer. The ultrasonic oscillations reflected from the surface of the article, in the form of a divergent beam, are received by two receiving ultrasonic transducers. The received ultrasonic oscillations are compared to obtain a difference signal; a detector head housing is then turned, depending on the magnitude and sign of said difference signal. As the difference signal disappears, the axis of the detector head housing becomes directed along a line normal to the surface of the article and the device serves for ultrasonic echo flaw detection and is provided with apparatus for maintaining constant the distance between the ultrasonic flaw detecting transducer and the surface of the article being checked; it also has apparatus for the orientation of the detector head, which slides over the surface of the article, around the point at which ultrasonic oscillations are applied, and for a deflection of the ultrasonic flaw detecting transducer from the normal by an angle to direct the ultrasonic beam refracted in a line material of the article along a line normal to the surface of the flaw.

4 Claims, 8 Drawing Figures

METHOD OF ULTRASONIC ECHO FLAW DETECTION AND DEVICE FOR EFFECTING SAME

The present application is a continuation-in-part of Application Ser. No. 281,010 filed on Aug. 16, 1972. and now abandoned.

The present invention relates to improvements in flaw detection methods and apparatus and, more particularly, to a method of ultrasonic echo flaw detection and to a device for effecting the same. The invention is applicable, for example, in detecting flaws in different types of blanks of articles intended for operation under critical conditions.

There is widely known in the art a method of ultrasonic echo flaw detection, whereby an ultrasonic beam is directed at an article being checked, perpendicularly to its surface. After the ultrasonic pulses are reflected from the surface and internal layers of the article being checked, these pulses are received and converted into electric oscillations which contain information on flaws in the article. The foregoing method makes it necessary to maintain constant the distance between the surface of the article being checked and the ultrasonic flaw detecting transducer.

In order to ensure the entry of the ultrasonic beam into the article being checked prependicularly, the article is subjected to preliminary machining, whereby some portions of it are formed with flat surfaces. The preliminary machining necessitates an additional allowance, apart from the normal machining allowance, in the blank, for example, a punched blank, which accounts for an increased waste of costly materials.

The preliminary machining must be very accurate; this, however, is a labor-consuming process which requires a number of machine tools specially assigned for the job.

There are known methods whereby ultrasonic oscillations are directed perpendicularly to the surface of an article being checked with the aid of tracer means or templates. When employing templates whose shape corresponds to the configuration of an article being checked, the profile of the article being checked is followed by a roller rolling along the template surface. In other flaw detection devices, the function of the rollers is performed by special programming systems. In some cases the profile of an article being checked is traced by contact gauges sliding along the surface of the article, whereas the longitudinal displacement of said gauges is registered by different types of pickups, for example, capacity transducers, inductance pickups, etc.

There are also known flaw detection devices wherein detection heads are oriented by comparing the distances from the center of the irradiating surface of the detection head to the surface of an article being checked, which distances are measured at a number of points with the aid of ultrasonic oscillations or by other means.

None of the foregoing methods provides a sufficiently accurate orientation of the detector head normal to the surface of an article being checked, because when templates are employed, it is impossible to take into account variations in the article dimensions within the predetermined allowance; additionally the surface profile of the article being checked is determined from the positions of several points leads to averaging the surface curvature of the article being checked, which also introduces a certain error. The latter disadvantage is also inherent in the method in which the article profile is traced with the aid of contact gauges; in addition, the latter method requires high machining accuracy of the article being checked.

Finally, a beam directed normal to the surface of an article mainly detects metallurgical defects located parallel to the article's surface. As a rule, other defects remain undetected, which reduces the checking accuracy.

It is an object of the present invention to provide a method of ultrasonic echo flaw detection and a device for effecting this method, which make it possible to detect flaws in a blank whose shape is maximally close to that of a finished article, without any special machining to form flat portions on the surface being checked, and to detect flaws with different orientation and, consequently, raise the reliability of checking.

The foregoing object is attained by providing a method of ultrasonic echo flaw detection effected, according to the invention, with the aid of an echo flaw detector and an ultrasonic flaw detecting transducer, whereby ultrasonic oscillation pulses are directed at an article being checked with the aid of the ultrasonic flaw detecting transducer; the pulses that are reflected from said article and carry information on flaws in said article are received; said to ultrasonic flaw detecting transducer and said article are mutually displaced for scanning the article by ultrasonic oscillations; in the course of checking, at the point at which are applied ultrasonic oscillations generated by the ultrasonic flaw detecting transducer, which effects flaw detection, there are directed at an angle, with the aid of a side focusing ultrasonic transducer, ultrasonic oscillations which are focused at that point, reflected in the form of a divergent beam, and received by two receiving ultrasonic transducer arranged in a plane perpendicular to the direction of the reflected ultrasonic oscillations, symmetrically relative to the longitudinal axis of a detection head; said oscillations are compared to obtain a different signal; depending upon the magnitude and sign of the difference signal, the detector head is turned in the plane of its displacement around the point of application of ultrasonic oscillations sliding over the surface of the article being checked, in order to decrease and then reduce to zero said difference signal, as the detector head is positioned perpendicularly to the surface of the article being checked; in order to direct ultrasonic oscillations at an angle which ensures perpendicular incidence of the ultrasonic beam with respect to the plane of a flaw found under the curvilinear surface of the article and oriented parallel to flat surfaces thereof, the ultrasonic flaw detecting transducer is deflected along curved guides of the detector head housing by an angle required to fulfil the foregoing condition.

The foregoing method is effected with the aid of a device comprising an ultrasonic echo flaw detector with a timer to whose outputs are connected an electric pulse generator and a scanning generator; and indicator of the ultrasonic echo flaw detector one of whose inputs is connected to the scanning generator, whereas its other input is connected to an output of an amplifier, an input of the amplifier being connected to an output of said electric pulse generator; a special detector head with an ultrasonic flaw detecting transducer movable in curved guides of the detector head housing and connected to an output of said electric pulse generator; a side focusing ultrasonic transducer rigidly mounted on the detector head housing so that the focused ultrasonic oscillation beam sent by said side focusing ultrasonic transducer is directed at the point whereat there are applied ultrasonic oscillations sent by the ultrasonic flaw detecting transducer, said side focusing ultrasonic transducer being connected to an electric pulse master generator of a servosystem constituted by a means for following up the surface profile and a means for maintaining a constant distance between the ultrasonic flaw detecting transducer and the surface of an article being checked with an actuating mechanism; two receiving ultrasonic transducers of said ultrasonic echo flaw detector, rigidly mounted on the detector head housing and arranged symmetrically with respect to the longitudinal axis of the special detector head so that the ultransonic oscillations reflected from the surface of the article being checked, which ultrasonic oscillations are irradiated by the side focusing ultransonic transducer in the form of a divergent beam, are directed perpendicularly to the surface which receives said reflected ultransonic oscillations, said two receiving ultrasonic transducers being connected to the means for following up the surface profile of the article being checked, which ensures rotation of the special detector head about the point at which the ultrasonic oscillations are directed, sliding over the surface of the article being checked; said receiving ultrasonic transducer being connected to the means for maintaining a constant distance between the ultrasonic flaw detecting transducer and the surface of the article being checked, which means ensures displacement of the special detector head in a vertical plane.

In order to ensure rotation of the detector head about the point of entry of ultrasonic oscillations and deflect the operating piezoconverter from a line normal to the surface of the article being checked by an angle corresponding to the fulfilment of the foregoing condition, it is expedient that the actuating mechanism be made up of two links one of which is rigidly coupled to the special detector head and transmits movement of a reversible electromotor to the means for following up the surface profile of the article being checked, thereby turning the special detector head about the point of entry of ultrasonic oscillations, whereas the other link is hingedly coupled to the ultrasonic flaw detecting transducer movable along the curved guides of the detector head housing and to a cam whose profile is such that the deflection angle of the ultrasonic flaw detecting transducer at any point of the curvilinear surface of the article being checked is set so that the ultrasonic oscillation beam refracted in the material of the article being checked is directed perpendicularly to the surface of a flaw located under said curvilinear surface of the article being checked and oriented parallel with flat surfaces thereof.

The proposed method and device for effecting the invention is advantageous in that at any portion of an article being checked, irrespective of the shape thereof, the ultrasonic beam is directed with sufficient accuracy along the normal to the surface of the article being checked or at a predetermined angle to that surface.

Other objects and advantages of the present invention will become more apparent from the following detailed description of a preferred embodiment thereof to be read in conjunction with the accompanying drawings, wherein.

Figure 5:
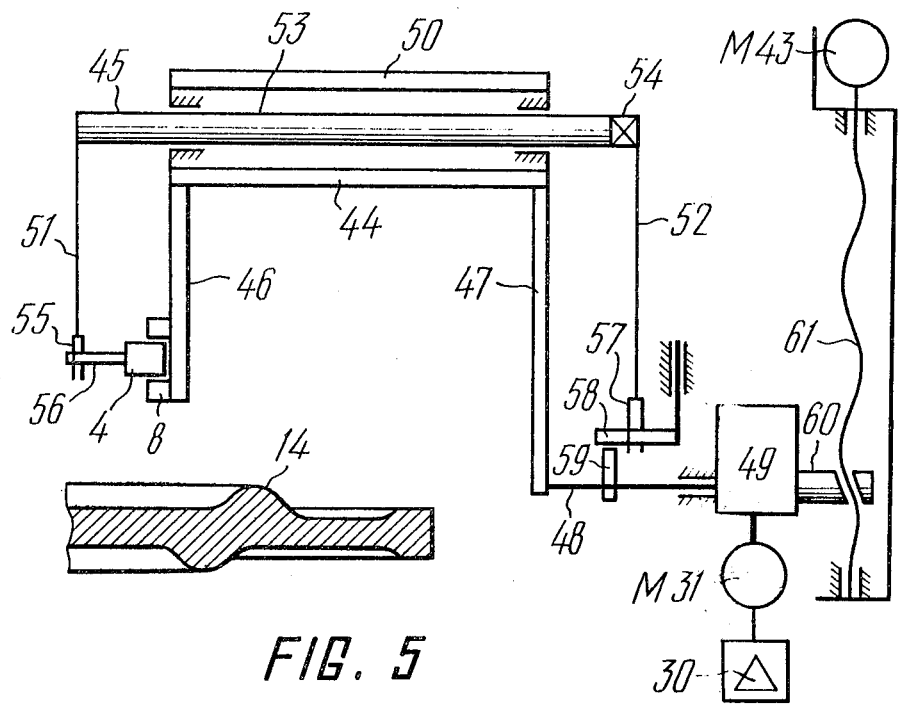
Figure 6:
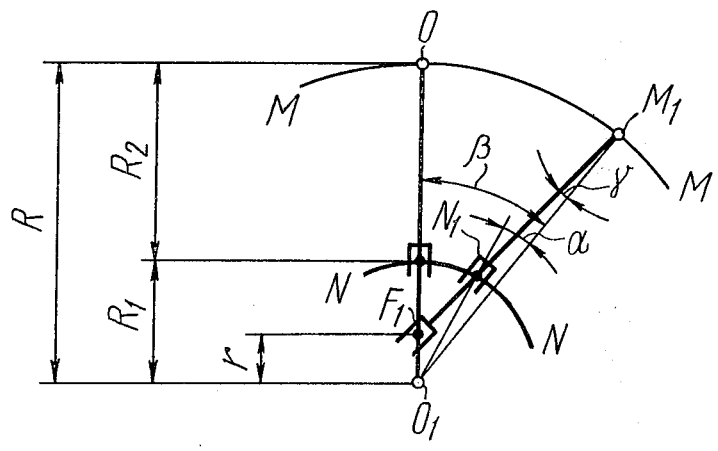
Figure 7:
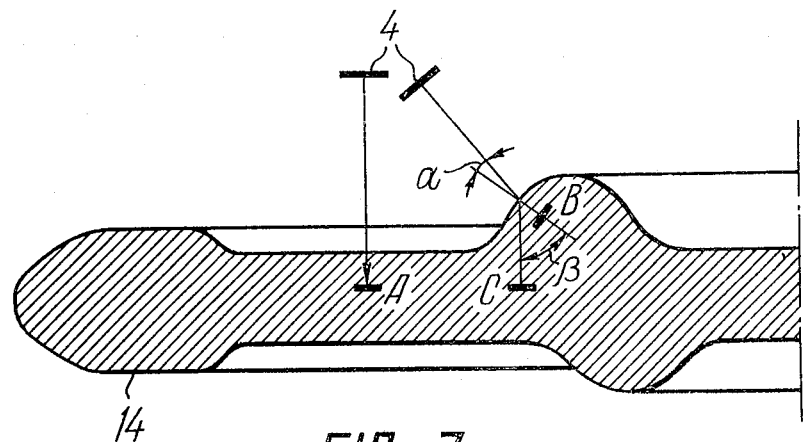

FIG. 5 diagrammatically shows the actuating mechanism of the system for orienting the field axis of the ultrasonic flaw detecting transducer in the ultrasonic flaw detection device;

FIG. 6 diagrammatically shows the plot of the cam profile;

FIG. 7 is a sectional view of an article being checked; and

Figure 8:
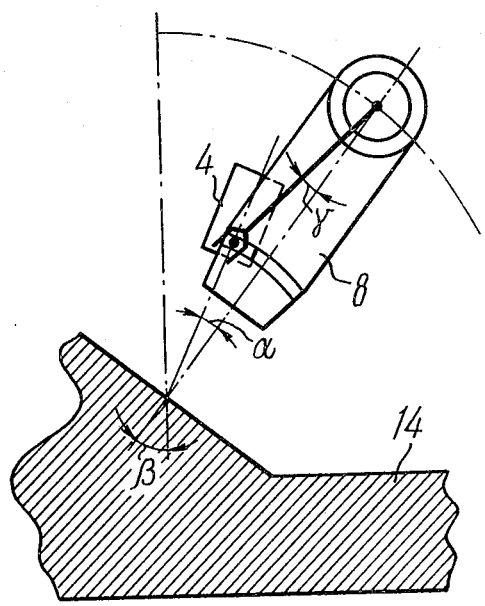

FIG. 8 shows the arrangement of the head and the ultrasonic flaw detecting transducer with respect to the article being checked.

Figure 2:
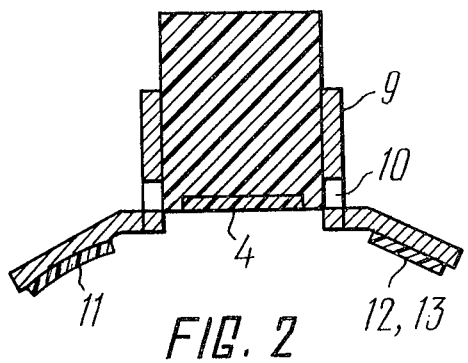
FIG. 2 shows the arrangement of ultrasonic transducer of the servosystem and the ultrasonic flaw detecting transducer in the detector head in a section along the detector head axis.
Figure 3:
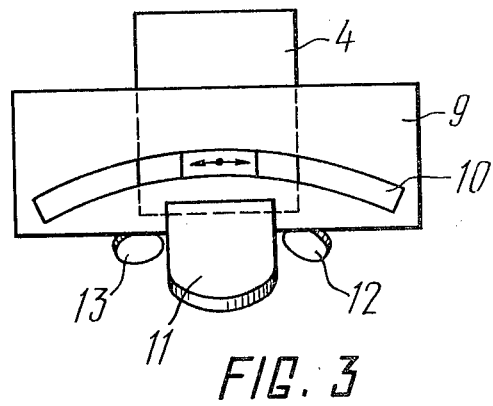
FIG. 3 is a side view of the arrangement of the ultrasonic transducer of the servosystem and the ultrasonic flaw detecting transducer in the detector head.
Figure 4:
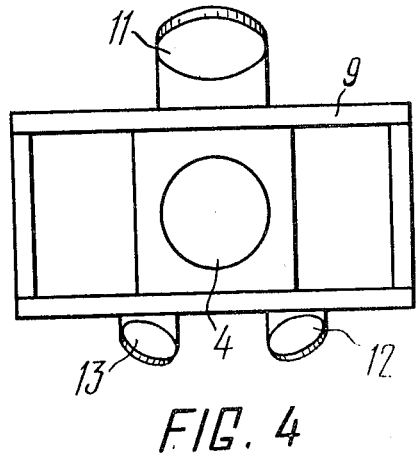
FIG. 4 is a bottom view of the arrangement of the ultrasonic transducer of the servosystem and the ultrasonic flaw detecing transducer in the detector head.

Referring now to the accompanying drawings, the proposed device for ultrasonic echo flaw detection comprises an ultrasonic flaw detector 1 (FIG. 1) which incorporates a timer 2 connected to an electric pulse generator 3 which excites a piezoelectric converter serving as an ultrasonic flaw detecting transducer 4. A scanning generator 5 of said ultransonic flaw detector 1 is electrically coupled via its input to an output of the timer 2 and via its output, to one of the inputs of an indicator 6. Connected to an output of the electric pulse generator 3 is an input of an amplifier 7 whose output is connected to another input of the indicator 6. The ultrasonic flaw detector has a detector head 8 (FIGS. 2, 3 and 4) which includes a detector head housing 9, carrying the ultrasonic transducer 4 which for reasons of brevity is referred to further in the text of the disclosure as a "finder". The finder 4 is movable in curved guides 10 of the detector head 8 which further includes a focusing ultrasonic transducer 11 of a servosystem, which transducer 11 is rigidly mounted on the housing 9 of the detector head for joint movement therewith. Two receiving ultrasonic transducers serving as ultrasonic flaw detecting transducers 12 and 13 of the servosystem are also rigidly mounted on the housing 9 and are arranged symmetrically with respect to the longitudinal axis thereof. The system for orienting the detector head 8 with the servomechanism comprises a link means for moving the finder 4 is the guides 10 of the housing 9 of the detector head 8 and a means for maintaining a constant distance between the detector head 8 and the surface of an article 14 being checked.

The system for orienting the detector head (FIG. 1) comprises a delay line 15 connected to the timer 2. Connected to an output of the delay line 15 are a servosystem master generator 16 exciting the transducer 11, a unit 17 for suppressing a sounding pulse, and serially interconnected multivibrators 18 and 19. Connected in parallel to an output of the multivibrator 19 are time selectors 20 and 21 which serve to discriminate a tracing pulse arriving from amplifiers 22 and 23 whose inputs are connected to the transducers 12 and 13. Connected before the inputs of the amplifiers 22 and 23 is a potentiometer 24 for levelling the amplitudes of signals applied to the amplifiers. Connected to outputs of the time selectors 20 and 21 are detectors 25 and 26 of different polarity, and detectors 27 and 28 of the same polarity. The other terminals of the detectors 25 and 26 are connected to an input of an adder 29 whose output is connected to an input of a phase-sensitive amplifier 30 which controls a reversible electromotor 31 which, by means of an actuator (shown by a dot-and-dash line in FIG. 1) turns the detector head about the point of entry of ultrasonic oscillations sliding over the surface of the article 14.

The means for maintaining a constant distance between the detector head 8 and the surface of the article 14 comprises the unit 17 for suppressing the sounding pulse connected to the delay line 15, an output of said unit 17 being connected to a flip-flop 32 and a multivibrator 33. The flip-flop 32 is connected to an input of a blocking oscillator 34 for actuating the latter and to an output of an adder 35 to which are applied distance tracking signals. Inputs of the adder 35 are connected via the detectors 27 and 28 to outputs of the time selectors 20 and 21. The flip-flop 32 is also connected via a delay line 36 to a multivibrator 37 for actuating the latter and to an input of a time selector 38. An output of the multivibrator 37 generating a gate is connected to an input of a time selector 39. An output of the blocking oscillator 34 is connected to another arm of the time selectors 38 and 39 which form a distance tracking zone, outputs of said time selectors 38 and 39 being connected via detectors 40 and 41 to an input of a phase sensitive amplifier 42 which controls a reversible electromotor 43 for moving the detector head 8 in the vertical plane.

The actuating mechanism of the orienting system is shown in FIG. 5. This mechanism comprises the controlled reversible electromotor 31 and two links 44 and 45; the link 44 is rigidly coupled to the head 8 (see FIG. 1) and transmits movement of the reversible electromotor 31 for orienting the detector head 8 along the normal to the surface of the article 14, whereas the other link 45 is hingedly coupled to the finder 4 and to deflect said finder 4 by a preselected angle with respect to the normal. Each link 44 and 45 is constructed as a pair of legs joined by means of a connection strip.

In the inverted U-shaped link 44 one side leg 46 is coupled to the head 8, whereas a second side leg 47 is coupled via an axle 48 and a reduction gear 49 to the electromotor 31. A connection strip 50 of the link 44, which joins the side legs 46 and 47, is constructed as a hollow tube.

The second link 45 is formed by side legs 51 and 52 joined by a connection strip 53. The side leg 52 is coupled to the connection strip 53 by means of a clutch 54.

Mounted on the side leg 51 is a fork 55 interacting with a pin 56 rigidly coupled to the finder 4. Mounted on the side leg 52 is a fork 57 interacting with a pin 58 which moves under the action of a cam 59 in the vertical plane. The cam 59 is mounted on the axle 48; the profile of said cam must ensure the fulfilment of the following condition:

$$\frac{\sin\alpha}{\sin\beta} = \frac{C_1}{C_2} = n,$$

where $\alpha$ is the angle of incidence of the ultrasonic beam on the article being checked;

$\beta$ is the angle of refraction of the beam in the article;

$C_1$ is the propagation velocity of ultrasound in the contact medium;

$C_2$ is the propagation velocity of ultrasound in the article being checked;

$n$ is the refractive index for the given contact medium and the material of the article being checked.

Instantaneous values of radii $r$ of the cam 59 may be found by the formula:

$$r = \frac{nR_1(F_1M_1)}{(E_1M_1)}$$

where $R_1$ is the radius of curvature of the guides 10, equal to a distance between the point of entry of ultrasonic oscillations into the article and the irradiating surface of the finder 4;

$F_1M_1$ (FIG. 6) is the instantaneous value of the distance between the axis of the connection strip 53 and the axis of the pin 58 with a turn of the axis of the reduction gear 49 and cam 59 by an angle $\gamma$ which corresponds to setting the head 8 normal to the surface of the article 14;

$E_1M_1$ is the instantaneous value of the distance between the axis AA of the connection strip 53 and the axis of the pin 56 (FIG. 5) at the moment the finder 4 is deflected by an angle $\alpha$, which ensures fulfilment of the condition:

$$\frac{\sin\alpha}{\sin\beta} = \frac{C_1}{C_2} = n.$$

The instantaneous values of the radius $r$ may be established graphically, as is shown in FIG. 6.

Plotted (to scale) on the vertical line $00_1$ is the value $R$ equal to the distance between the axis AA of the connection strip 53 and the point of entry of the ultrasonic beam into the article. This is followed by describing from point $0_1$ arcs MM and NN having radii R and $R_1$, respectively. Depending upon the curvature, the surfaces of the article's portions are set by angles $\beta$ which ensure setting the finder 4 normal to the curvilinear surface. From point $0_1$ a radius is then described at an angle $\beta$ until its intersection at point $M_1$ with the arc MM. The value of the angle $\alpha$ is calculated from the relation $$\frac{\sin\alpha}{\sin\beta} = \frac{C_1}{C_2} = n,$$

and from point $0_1$ a radius is described at an angle $\alpha$ to the straight line $0_1M_1$ until it intersects at point $N_1$ with the arc NN. A straight line is then drawn through points $M_1$ and $N_1$ until it intersects the straight line $00_1$. The portion $0_1F_1$ corresponds to the instantaneous value of the radius $r$ of the cam 59, whereby the condition $$\frac{\sin\alpha}{\sin\beta} = \frac{C_1}{C_2} = n$$

is fulfilled for a preselected curvature of a portion of the article being checked.

Taking different values of the angle $\beta$, one can determine the profile of the cam 59.

A carriage 60 (FIG. 5), which supports the detector head 8 and the links 44 and 45, is mounted on a motion screw coupled to the electromotor 43. Rotation of the motion screw 61 ensures a constant distance between the finder 4 and the point of entry of the ultrasonic beam into the article 14.

The operation of the proposed device for ultrasonic flaw detection will next be given. The description of this operation is intended to explain in greater detail the essence of the proposed method.

The detector head 8 (FIG. 1) is set in the initial position at which the irradiation axis of the finder 4 is perpendicular to a flat surface of the article 14 being checked. The slide of the potentiometer 24 is set so that the voltages across the outputs of the amplifiers 22 and 23 are equal.

Figure 1:
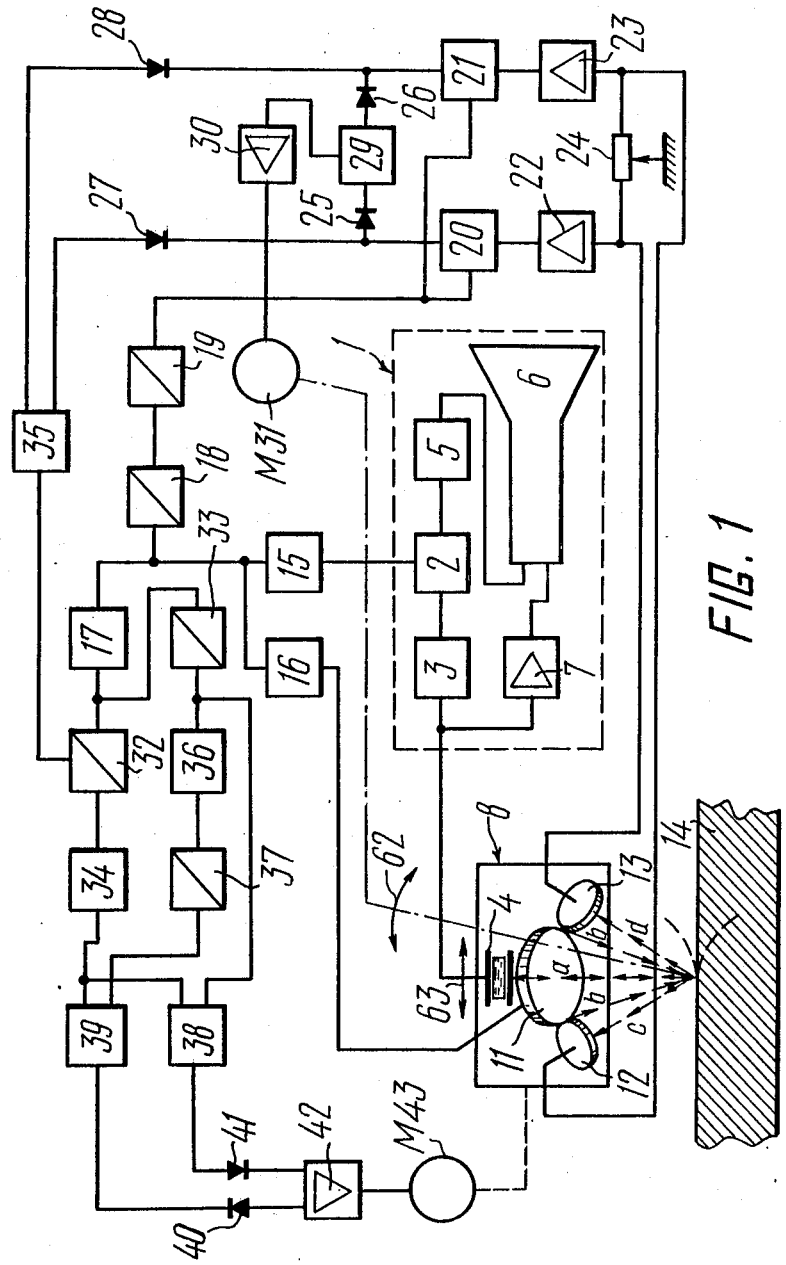
FIG. 1 is a block diagram of a system for orienting the field axis of the ultrasonic flaw detecting transducer in the proposed ultrasonic echo flaw detection device.

The pulse sent by the finder 4 of the detector head 8 is partially reflected from the surface of the article 14 being checked and the internal non-uniformities of (flaws) thereof in the form of an ultrasonic beam $a$ carrying information on the presence of flaws in said article 14 (FIG. 1).

From the delay line 15 the pulse is applied to the multivibrator 18 which actuates, with the trailing edge of the differentiated pulse, the multivibrator 19. From the multivibrator 19 the square pulse is applied to the coincidence circuit made up by the time selectors 20 and 21. Applied to the same coincidence circuit are pulses from the ultrasonic transducers 12 and 13 of the detector head 8, which pulses are applied via the amplifiers 22 and 23. The time selectors 20 and 21 have output circuits at which signals are taken and applied via the detectors 25 and 26 of different polarity to the adder 29, after which the difference signal is applied to the input of the phase-sensitive amplifier 30 which controls the reversible electromotor 31.

As the beam is reflected from the flat surface, the signals at the ultrasonic transducers 12 and 13 are equal. If the orientation of the reflecting surface of the article 14 is changed, the reflected pulse is correspondingly deflected and follows the path of the beam $c$ or $d$; as a result, the ultrasonic transducers 12 and 13 receive pulses having different amplitudes.

If the detector head 8 is moved over the surface of the article 14 being checked without changing the orientation of said detector head 8, the voltage across the output of the amplifier 30 remains equal to zero as long as the surface of the article 14 being checked remains flat. But when the detector head 8 reaches a point where the flat surface joins a curvilinear surface, a signal is applied to one of the receiving ultrasonic transducers, which signal is different from the one applied to the other transducer. Hence, the electric signals at the outputs of the ultrasonic transducers 12 and 13 are different. As a result, there appears a difference signal at the output of the amplifiers 22 and 23. Depending upon the magnitude and sign of this signal, there appears a voltage across the output of the phase-sensitive amplifier 30, the magnitude and polarity of said voltage being determined by the curvature of the curvilinear surface of the article 14 and the sign of that curvature. Said voltage is applied to the control circuit of the reversible electromotor 31 which ensures, with the aid of the actuating mechanism (conventionally shown by the dot-and-dash line in FIG. 1), rotation of the detector head 8 around the point of entry of ultrasonic oscillations into the article 14 in the plane of its movement, as is shown by the arrow 62, in order to reduce the error signal.

As the detector head 8 is turned and as its axis approaches a line normal to the curvilinear surface, at a given point the difference becomes smaller between the signals applied to each of the ultrasonic transducers 12 and 13. When equal signals are applied to each of said ultrasonic transducers, the axis of the detector head 8 coincides with the normal to the surface of the article 14 being checked. At this moment the voltage across the output of the phase-sensitive amplifier 30 becomes equal to zero, and the rotation of the electromotor 31 is stopped.

The system for maintaining a constant distance between the finder 4 and the surface of the article 14 operates as follows. The pulse which is taken off the timer 2 and passes through the delay line 15 is applied to the unit 17 for suppressing the sounding pulse and then to one of the arms of the flip-flop 32 and actuates the latter.

The signals received by the ultrasonic transducers 12 and 13 are applied to the amplifiers 22 and 23 and are then applied via the time selectors 20 and 21 and the detectors 27 and 28 to the input of the adder 35 from whose output they are applied to the flip-flop 32 and set it into one of its stable states. The flip-flop 32 then actuates the blocking oscillator 34 whose pulse is applied to the time selectors 38 and 39.

From the output of the unit 17 for suppressing the sounding pulse there is applied a pulse to the multivibrator 33 which generates a square forward gating pulse applied to the time selector 38. The same pulse passes through the delay line 36, whose delay time is equal to the duration of the pulse of the blocking oscillator 34, and actuates the multivibrator 37 which generates a square rear gating pulse applied to the time selector 39.

If the pulse arriving from the blocking oscillator 34 is located in time between the first and second gates arriving from the multivibrators 33 and 37, there is no signal at the outputs of the time selectors 38 and 39 and, consequently, the voltage across the output of the phase-sensitive amplifier 42 is equal to zero. If the distance between the detector head 8 and the surface of the article 14 being checked is changed, the pulse arriving from the blocking oscillator 34 coincides in time with one of the gates arriving from the multivibrator 33 or multivibrator 37; as a result, the time selectors 38 and 39 send to the phase-sensitive amplifier 42 via the detectors 40 and 41 a signal of positive or negative polarity, correspondingly. At the output of the phase-sensitive amplifier 42 at the start of the phase of the respective polarity there appears alternating voltage which causes the electromotor 43 to move in one or other direction and displace the detector head 8 in the vertical plane.

As a result of adding the displacement of the detector head 8 about its axis to the uniform horizontal motion thereof along the surface of the article 14 and the rotation thereof about the point of entry of ultrasonic oscillations, which point slides over the surface of the article 14, the trajectory of the movement of the detector head 8 is expressed by a line equidistant to said surface, which corresponds to the optimum checking conditions.

In case the finder 4 is rigidly fixed in the detector head 8, the foregoing method is effective for detecting flaws A and B (FIG. 7) oriented perpendicularly to the normal at the point of entry of utrasonic oscillations into the article 14 being checked. In this case the detector head 8 is rigidly coupled, via the reduction gear 49, to the shaft of the electromotor 31, and the field axis of the finder 4 is oriented by turning the detector head 8.

However, when checking articles of complex configuration, there arises the necessity of detecting flaws C (FIG. 7) located under curvilinear portions of the surface of the article 14 being checked and parallel to flat surfaces thereof. For this purpose it is necessary to deflect the axis of the ultrasonic field of the finder 4 by an angle which ensures the incidence of the ultrasonic beam refracted in the article 14 along the normal to the surface of the flaw C. This conditon is met if $$\frac{\sin\alpha}{\sin\beta} = \frac{C_1}{C_2} = n.$$

Thus, the actuating mechanism must ensure the setting of the detector head 8 (FIG. 8) along the normal to the surface of the article 14 being checked, and the turning of the finder 4 with respect to the normal by an angle $\alpha$.

The detector head housing 10 is provided with curved guides whose radius is equal to the distance between the irradiating surface of the finder 4 and the point of entry of the ultrasonic beam into the article 14. The finder 4 is installed in a holder (not shown) moving in said direction. Thus, while setting the detector head 8 along the normal to the surface of the article 14 being checked, the finder 4 can be turned by a certain angle $\alpha$ relative to the normal for adjusting the incidence angle of the ultrasonic beam entering the article 14.

The actuating mechanism of the orientation system shown in FIG. 5 operates as follows.

The finder 4 is set along the normal to the surface of the article 14 being checked. The clutch 54 is unlocked, whereby the link 45 is put out of action. By moving carriage 60 with the aid of the screw 61, the finder 4 is set at a preset distance from the flat surface of the article 14. The carriage, which carries the orientation system, is moved along the article 14 being checked as is shown by the arrow 63 (FIG. 1). The device for ultrasonic echo flaw detection operates as described above. As a signal appears at the output of the amplifier 30, the electromotor 31 sets into rotation, via the reduction gear 49, the axle 48 (FIG. 5). This causes the link 44 to turn, whereby the detector head 8 is turned as long as the amount of energy reflected from the surface of the article 14 and received by both ultrasonic transducers 12 and 13 is not equal, which means that the finder 4 is not arranged along the normal to the surface of the article 14. As the amounts of energy received by the two ultrasonic transducers 12 and 13 become equal, the signal at the output of the amplifier 30 disappears, and the link 44 stops turning. In this way flaws of the A and B types are detected (FIG. 7).

In order to detect flaws of the C type, the clutch 54 is brought into play. As this takes place, only curvilinear portions of the surface of the article 14 are scanned. During this process the link 44 sets the detector head 8 at each point of the curvilinear surface along the normal to the article 14; the link 45 is turned under the action of the cam 59 and displaces the finder 4 in the curved guides 10 by an angle $\alpha$ determined by the radius r of the cam 59. In this way flaws of the C type are detected.

The use of the present invention, for example, in checking punched blanks for turbine discs from refractory alloys greatly raises the reliability of checking, as it makes it possible to detect flaws with different orientation. In addition, the use of this invention makes it possible to reduce the punching allowance.

What is claimed is:

1. A method of ultrasonic echo flaw detection of articles, with an echo flaw detector having a detecting head carrying an ultrasonic flaw detecting transducer, said method comprising directing ultrasonic oscillation pulses at an article being checked by the ultrasonic flaw detecting transducer; receiving pulses reflected from the surface of said article and carrying information on the presence of flaws in said article; relatively displacing said head and ultrasonic flaw detecting transducer with respect to said article for scanning the article with ultrasonic oscillations; directing additional ultrasonic oscillations at said article at an angle at the point of entry of the ultrasonic oscillations emitted by the ultrasonic flaw detecting transducer, receiving the additional ultrasonic oscillations as a reflected divergent beam by two further ultrasonic transducers arranged in a plane perpendicular to the direction of the reflected ultrasonic oscillations and symmetrically with respect to the longitudinal axis of the detector head; comparing said additional oscillations to obtain a difference signal; turning the detector head in the plane of its displacement around the point of entry of ultrasonic oscillations, in proportion to the magnitude and sign of the difference signal, to decrease and ultimately reduce to zero the difference signal as the detector head approaches a line normal to the surface of the article; and displacing the ultrasonic flaw detecting transducer along a curvilinear path to direct ultrasonic oscillations at an angle to said article to insure the incidence of the ultrasonic beam perpendicular to the plane of a flaw found under a curvilinear surface of the article and oriented parallel to its flat surfaces.

2. Apparatus for ultrasonic echo flaw detection of articles, said apparatus comprising a turnable detector head, means supporting said head for undergoing relative displacement with respect to an article for flaw detection thereof, said head having a longitudinal axis, an ultrasonic flaw detecting transducer mounted on said head for directing a beam of ultrasonic oscillation pulses to said article and for receiving reflected pulses carrying information on the presence of flaws in the article, a second transducer carried by said head for directing a second beam of ultrasonic pulses at said article at the point of contact of the first beam with the surface of said article and at an angle with said first beam, said second beam being reflected from said article as a divergent beam, two further transducers disposed in a plane perpendicular to the direction of the reflected beam of ultrasonic oscillations and symmetrically with respect to the longitudinal axis of the detector head to receive the reflected divergent beam, comparator means connected to said two further transducers for comparing the reflected signals received thereby to produce a difference signal when said reflected signals differ, means for turning said detector head in the plane of its relative displacement with respect to the article about said point of contact in proportion to the magnitude and sign of the difference signal to nullify said signal and position said longitudinal axis perpendicular to the surface of the article, said head having guide grooves receiving said flaw detecting transducer for displacement therein and means for displacing the flaw detecting transducer in said guide grooves to direct the beam of ultrasonic oscillations at an angle when the surface of the article is curved such that the beam is perpendicular to the plane of a flaw under said surface.

3. Apparatus for ultrasonic flaw detecting comprising an ultrasonic flaw detector including a timer having two outputs, an electric pulse generator connected to one of the timer outputs, a scanning generator connected to the other of the timer outputs, an ultrasonic flaw detector indicator having one input connected to the output of the pulse generator, a detector head including an ultrasonic flaw detecting transducer connected to the output of the pulse generator, said detector head having a housing with a longitudinal axis and curved guide slots in which said transducer is displaceable, means for providing relative displacement between said head and the article under test, a second transducer rigidly mounted on said housing to direct a beam at the point of entry of the ultrasonic beam from the first transducer in the article under test, follow-up means for following the surface profile of the article under test and for maintaining a constant distance between the first transducer and the surface of the article under test, said follow-up means including a further electric pulse generator connected to said second transducer, and an actuating mechanism, two additional receiving transducers rigidly mounted on the housing of the detector head and arranged symmetrically with respect to the longitudinal axis of the housing such that ultrasonic oscillations emitted from the second transducer and reflected by the article under test are received by the receiving transducers perpendicularly to the receiving surfaces thereof, means pivotally supporting said head for movement about said point of entry, said receiving transducers being connected to said follow-up means to operate said actuating mechanism to pivot the detector head about said point of entry as the head moves relative to the surface of the article while maintaining a constant distance between the first transducer and the surface of the article to insure relative displacement between the head and the article in a vertical plane.

4. Apparatus as claimed in claim 3 wherein said actuating mechanism includes two links, one rigidly connected to the detector head, a first motor connected to said one link to pivot said head about said point of entry, the second link being pivotally connected to said first transducer, and a cam coupled to said second link to move said first transducer in said curved guide slots, said cam having a surface profile to make the angle of deflection of the first transducer at any point on a curvilinear surface of the article under test such that the ultrasonic beam reflected in the article is directed along a line perpendicular to the surface of a flaw under the surface of the article.

* * * * *